United States Patent
Patel et al.

(10) Patent No.: US 10,596,138 B2
(45) Date of Patent: Mar. 24, 2020

(54) REDUCED FAT, SHELF STABLE LIQUID NUTRITIONAL COMPOSITION

(71) Applicant: Abbott Laboratories, Abbott Park, IL (US)

(72) Inventors: Gaurav Patel, Gahanna, OH (US); Tapas Das, Worthington, OH (US); Rockendra Gupta, Columbus, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 15/760,471

(22) PCT Filed: Sep. 13, 2016

(86) PCT No.: PCT/US2016/051508
§ 371 (c)(1),
(2) Date: Mar. 15, 2018

(87) PCT Pub. No.: WO2017/048708
PCT Pub. Date: Mar. 23, 2017

(65) Prior Publication Data
US 2018/0250258 A1     Sep. 6, 2018

Related U.S. Application Data

(60) Provisional application No. 62/219,436, filed on Sep. 16, 2015.

(51) Int. Cl.
| | |
|---|---|
| A61K 31/00 | (2006.01) |
| A61K 9/107 | (2006.01) |
| A23L 33/12 | (2016.01) |
| A23L 33/105 | (2016.01) |
| A61K 31/202 | (2006.01) |
| A23L 33/16 | (2016.01) |
| A23L 33/17 | (2016.01) |
| A23L 33/10 | (2016.01) |
| A23L 33/00 | (2016.01) |
| A23L 33/115 | (2016.01) |
| A23L 33/125 | (2016.01) |
| A61K 31/047 | (2006.01) |
| A61K 31/19 | (2006.01) |
| A61K 33/30 | (2006.01) |

(52) U.S. Cl.
CPC ............ *A61K 31/202* (2013.01); *A23L 33/10* (2016.08); *A23L 33/115* (2016.08); *A23L 33/12* (2016.08); *A23L 33/125* (2016.08); *A23L 33/16* (2016.08); *A23L 33/17* (2016.08); *A23L 33/40* (2016.08); *A61K 31/047* (2013.01); *A61K 31/19* (2013.01); *A61K 33/30* (2013.01); *A23V 2002/00* (2013.01)

(58) Field of Classification Search
CPC ........ A23L 33/10; A23L 33/15; A23L 33/115; A23L 33/12; A23L 33/125; A23L 33/16; A23L 33/17; A23L 33/40; A23D 9/007; A61K 31/122; A61K 31/047; A61K 31/19; A61K 31/202; A61K 33/30; A23V 2002/00

See application file for complete search history.

(56) References Cited

U.S. PATENT DOCUMENTS

| | | | | |
|---|---|---|---|---|
| 5,955,102 | A * | 9/1999 | Gorenbein | A61K 9/4858 424/441 |
| 2005/0249821 | A1* | 11/2005 | Paul, Jr. | A61K 8/671 424/638 |
| 2006/0088574 | A1 | 4/2006 | Manning et al. | |

FOREIGN PATENT DOCUMENTS

| | | |
|---|---|---|
| WO | 2012/112419 A1 | 8/2012 |
| WO | 2013/138157 A1 | 9/2013 |
| WO | 2014/152616 A1 | 9/2014 |
| WO | 2014/179526 A1 | 11/2014 |

OTHER PUBLICATIONS

Phillips (Adv Nutr 2015;6:452-60) (Year: 2015).*

* cited by examiner

*Primary Examiner* — Ernst V Arnold
(74) *Attorney, Agent, or Firm* — Porter Wright Morris & Arthur LLP

(57) ABSTRACT

Liquid nutritional compositions that include functional ingredients such as beta-hydroxy-beta-methylbutyrate, docosahexaenoic acid, and lutein are disclosed. The nutritional compositions are useful to promote at least one of physical performance (e.g., body composition, muscle mass, muscle strength) and cognitive function (e.g., focus, attention, alertness, executive function) in an individual. The functional ingredients are incorporated into the nutritional composition in such a way that they do not adversely affect the desirable properties of the nutritional composition such as, for example, nutritional value, stability, solubility, taste, and mouthfeel.

22 Claims, No Drawings

REDUCED FAT, SHELF STABLE LIQUID NUTRITIONAL COMPOSITION

FIELD

The present disclosure relates to nutritional compositions and methods of using the compositions for improving at least one of physical performance, cognition, or both. In particular, the nutritional compositions include beta-hydroxy-beta-methylbutyrate (HMB), docosahexaenoic acid (DHA), and lutein.

BACKGROUND

Liquid nutritional compositions typically include balanced amounts of macronutrients (proteins, carbohydrates, and fats), as well as micronutrients and flavorings. For example, nutrition shakes, i.e., non-carbonated liquid nutritional compositions which are intended for oral consumption and therefore have the consistency, flavor, and overall desirable sensory characteristics of common milk shakes, are widely-available consumer products. Examples include the Ensure®, Glucerna®, Myoplex®, and PediaSure® lines of nutrition shakes available from Abbott Nutrition of Columbus, Ohio, the Muscle Milk® line of nutrition shakes available from CytoSport, Inc. of Benicia, Calif., and the Resource® line of health shakes available from Nestle, S.A. of Vevey, Switzerland. Generally, these nutrition shakes are made up in the form of oil-in-water emulsions having the consistency of common milk shakes.

While attempts have been made in the past to introduce certain functional ingredients (e.g., ingredients that may promote physical performance over and above that provided by high quality macronutrient delivery) into liquid nutritional compositions and achieve the wide consumer acceptance of conventional nutritional compositions, this has yet to be accomplished as the resulting formulations often do not meet consumer expectations for taste, texture, etc. Accordingly, there is an unmet need for nutritional compositions that provide desirable functional ingredients while also delivering the experience that consumers have come to expect.

SUMMARY

The general inventive concepts are directed to liquid nutritional compositions comprising a combination of functional ingredients (e.g., beta-hydroxy-beta-methylbutyrate (HMB), docosahexaenoic acid (DHA), and lutein). The combination promotes at least one of physical performance (e.g., body composition, muscle mass, muscle strength), cognitive function (e.g., focus, attention, alertness, executive function), and combinations thereof in an individual. The functional ingredients are delivered in a nutritional composition that is shelf stable and delivers the consumer experience expected for a liquid nutritional beverage.

In an exemplary embodiment, a liquid nutritional composition is provided. The liquid nutritional composition comprises beta-hydroxy-beta-methylbutyrate in an amount of 0.25 g to 3 g per serving of the nutritional composition; docosahexaenoic acid in an amount of 32 mg to 2500 mg per serving of the nutritional composition; and lutein in an amount of 0.3 mg to 35 mg per serving of the nutritional composition.

Methods of improving at least one of physical performance (e.g., body composition, muscle function, muscle mass, muscle strength), cognitive function (e.g., focus, attention, alertness, executive function), and combinations thereof, in an individual are also provided herein. The methods described herein include administering to an individual an effective amount of a composition comprising a source of beta-hydroxy-beta-methylbutyrate (HMB), a source of docosahexaenoic acid (DHA), and a source of lutein. Administration of the composition improves at least one of physical performance and cognitive function in an individual.

The nutritional compositions according to the general inventive concepts offer an alternative therapeutic or nutritional intervention option that can contribute to improvement in one or more of physical performance and cognitive function in an individual.

DETAILED DESCRIPTION

Much is known about the benefits of nutrients such as docosahexaenoic acid and lutein on the cognitive development of infants and children. However, less emphasis is placed on the potential benefits of particular nutrients on active or healthy adults. Therefore, there is an unmet need for a nutritional composition that can provide certain functional benefits (e.g., physical and cognitive benefits) to active or healthy adults. The general inventive concepts are directed to liquid nutritional compositions comprising a combination of functional ingredients including, but not limited to, beta-hydroxy-beta-methylbutyrate (HMB), docosahexaenoic acid (DHA), and lutein. The combination promotes at least one of physical performance (e.g., body composition, muscle mass, endurance, muscle strength), cognitive function (e.g., focus, attention, alertness, executive function), and combinations thereof, in an individual. The functional ingredients are delivered in a nutritional composition (e.g., a liquid nutritional beverage) that is shelf stable and delivers the consumer acceptance expected for a liquid nutritional beverage.

For the purposes of this disclosure, the following terms have the following meanings unless context dictates otherwise:

"Nutritional composition" refers to nutritional liquids, nutritional solids including nutritional powders which may be reconstituted to form a nutritional liquid, nutritional puddings, nutritional gels, nutritional bars, and other nutritional products all of which comprise one or more of protein, carbohydrate, and fat, and are suitable for oral consumption by a human.

The terms "administer," "administering," and "administration" as used herein, unless otherwise specified, should be understood to include providing a composition to an individual, the act of consuming a composition, and combinations thereof.

The term "effective amount" as used herein, unless otherwise specified, refers to a sufficient amount of a composition (e.g., a nutritional composition comprising a source of HMB, DHA, and lutein) to exhibit a therapeutic effect (e.g., improve physical performance, improve body composition, increase muscle function, increase cognition, increase focus, increase memory). The exact amount required to achieve the desired effect will vary from subject to subject, depending, for example, on the species, age, weight, lifestyle and general condition of the particular subject.

The terms "nutritional liquid," "liquid nutritional composition," and "liquid nutritional beverage" as used herein, unless otherwise specified, refer to nutritional compositions in ready-to-drink liquid form, concentrated liquid form, and nutritional liquids made by reconstituting nutritional powders described herein prior to use. The nutritional liquid may also be formulated as a suspension, an emulsion, a solution, and so forth.

The term "nutritional powder" as used herein, unless otherwise specified, refer to nutritional compositions in flowable or scoopable form that can be reconstituted with water or another aqueous liquid prior to consumption and includes both spray dried and drymixed/dryblended powders.

The term "nutritional semi-solid" as used herein, unless otherwise specified, refers to nutritional compositions that are intermediate in properties, such as rigidity, between solids and liquids. Some semi-solid examples include puddings, yogurts, gels, gelatins, and doughs.

The term "nutritional semi-liquid" as used herein, unless otherwise specified, refers to nutritional compositions that are intermediate in properties, such as flow properties, between liquids and solids. Some semi-liquid examples include thick shakes, liquid yogurts, and liquid gels.

The term "serving" as used herein, unless otherwise specified, refers to an amount which is intended to be consumed by an individual in one sitting or within one hour or less. Unless otherwise specified, when referring to a liquid nutritional composition, the term serving refers to an 8 oz. (e.g., ~237 mL) portion.

The terms "cognition" and "cognitive function" as used herein, unless otherwise specified, refer to the focus, attention, alertness, learning, thinking, and memory (i.e., memory acquisition, memory retention, and memory recall) of the brain. The term "improving cognition" as used herein, unless otherwise specified, refers to improving at least one of the focus, attention, alertness, learning, thinking, and memory functions of an individual.

The term "physical performance" as used herein, unless otherwise specified, refers to the body composition, endurance, muscle mass, and muscle strength of an individual. The term "improving physical performance" as used herein, unless otherwise specified, refers to improving at least one of the body composition, endurance, muscle mass, muscle function, and muscle strength of an individual.

The term "body composition" as used herein, unless otherwise specified, should be understood to refer to the ratio of lean body mass (i.e., muscle mass) to fat mass of the individual.

The term "muscle" as used herein, unless otherwise specified, refers to skeletal muscle, as well as other non-skeletal, striated muscles such as diaphragm, extraocular muscle, and so forth.

The term "muscle mass" as used herein, unless otherwise specified, refers to the amount or size of muscle or muscle groups, as expressed by muscle weight, mass, area, or volume. Muscle mass may also be expressed as total lean body mass, lean body mass of a body compartment such as the leg, or cross-sectional area of a leg or arm compartment. The volume or mass of the muscle can be determined using any known or otherwise effective technique that provides muscle area, volume, or mass, such as DEXA, or using visual or imaging techniques such as MRI or CT scans.

The term "muscle strength" as used herein, unless otherwise specified, refers to the amount of force a muscle, or muscle groups in sum, can exert. Muscle strength may be evaluated by a variety of methods such as grip strength, one repetition maximum strength test, time-dependent tests of muscle endurance, time-dependent tests of muscle fatigue, or time-dependent tests of muscle endurance and fatigue, and so forth.

The term "muscle function" as used herein, unless otherwise specified, refers to at least one of muscle mass and muscle strength.

"Shelf stable" refers to a liquid nutritional composition that remains commercially stable after being packaged and then stored at 18-24° C. for at least 3 months. Shelf stability may be measured by any suitable indicia of stability including, but not limited to, consumer acceptance panel, sedimentation, etc.

Beta-Hydroxy-Beta-Methylbutyrate (HMB)

HMB is a metabolite of the essential amino acid leucine. As used herein the terms HMB and beta-hydroxy-beta-methylbutyrate should be understood to include multiple forms or sources of HMB including, but not limited to, the free acid, salts, anhydrous salts, esters, lactones and other bioavailable forms of HMB suitable for oral administration. For example, in certain exemplary embodiments, the source of HMB is selected from the group consisting of: an ester of HMB; a lactone of HMB; a free acid of HMB; a salt of HMB; and combinations thereof.

One suitable form of HMB that may be utilized in the nutritional compositions described herein is the calcium salt of HMB, also designated as Ca-HMB, which is most typically the monohydrate calcium salt. Calcium HMB monohydrate is commercially available from Technical Sourcing International (TSI) of Salt Lake City, Utah. Non-limiting examples of other suitable salts of HMB (hydrated or anhydrous) for use herein include sodium, potassium, chromium, and other non-toxic salt forms. Unless specifically indicated otherwise, the amounts of HMB described herein are based on the assumption that the HMB is being provided as Ca-HMB monohydrate.

The amount of HMB present in the nutritional compositions can vary depending on the individual, the intended use, or both. In certain exemplary embodiments, the HMB is present in the nutritional composition at a concentration effective to improve one or more of physical performance and cognition in an individual. In certain exemplary embodiments, the liquid nutritional composition comprises HMB in an amount of 0.25 g to 3 g per serving of the nutritional composition. In certain exemplary embodiments, the liquid nutritional composition comprises HMB in an amount of 0.5 g to 3 g per serving of the nutritional composition. In certain exemplary embodiments, the liquid nutritional composition comprises HMB in an amount of 0.5 g to 2.5 g per serving of the nutritional composition. In certain exemplary embodiments, the liquid nutritional composition comprises HMB in an amount of 0.5 g to 2 g per serving of the nutritional composition. In certain exemplary embodiments, the liquid nutritional composition comprises HMB in an amount of 0.5 g to 1.5 g per serving of the nutritional composition. In certain exemplary embodiments, the liquid nutritional composition comprises HMB in an amount of 1 g to 3 g per serving of the nutritional composition. In certain exemplary embodiments, the liquid nutritional composition comprises HMB in an amount of 1 g to 2.5 g per serving of the nutritional composition. In certain exemplary embodiments, the liquid nutritional composition comprises HMB in an amount of 1 g to 2 g per serving of the nutritional composition. In certain exemplary embodiments, the liquid nutritional composition comprises HMB in an amount of about 1.5 g per serving of the nutritional composition.

Polyunsaturated Fatty Acids (PUFAs)

The nutritional compositions described herein include a polyunsaturated fatty acid (PUFA). In certain exemplary embodiments, the PUFA is an ω-3 PUFA. In certain exemplary embodiments, the PUFA is docosahexaenoic acid (DHA). In certain exemplary embodiments, the PUFA is provided as a free fatty acid, in triglyceride form, in diglyceride form, in monoglyceride form, in phospholipid form, or as a mixture of one or more of the above. Preferably, but not necessarily, the PUFA is provided in triglyceride form.

The amount of DHA present in the nutritional compositions can vary depending on the individual, the intended use, or both. In certain exemplary embodiments, the DHA is present in the nutritional composition at a concentration effective to improve one or more of physical performance and cognition in an individual. In certain exemplary embodiments, the liquid nutritional composition comprises DHA in an amount of 32 mg to 2500 mg per serving of the nutritional composition. In certain exemplary embodiments, the liquid nutritional composition comprises DHA in an amount of 50 mg to 2500 mg per serving of the nutritional composition. In certain exemplary embodiments, the liquid nutritional composition comprises DHA in an amount of 50 mg to 2000 mg per serving of the nutritional composition. In certain exemplary embodiments, the liquid nutritional composition comprises DHA in an amount of 50 mg to 1000 mg per serving of the nutritional composition. In certain exemplary embodiments, the liquid nutritional composition comprises DHA in an amount of 50 mg to 500 mg per serving of the nutritional composition. In certain exemplary embodiments, the liquid nutritional composition comprises DHA in an amount of 50 mg to 250 mg per serving of the nutritional composition. In certain exemplary embodiments, the liquid nutritional composition comprises DHA in an amount of 50 mg to 200 mg per serving of the nutritional composition. In certain exemplary embodiments, the liquid nutritional composition comprises DHA in an amount of 50 mg to 150 mg per serving of the nutritional composition. In certain exemplary embodiments, the liquid nutritional composition comprises DHA in an amount of about 125 mg per serving of the nutritional composition.

PUFAs, such as DHA, are known to oxidize over time in liquid nutritional compositions. Oxidation of PUFAs in liquid nutritional compositions can lead to reduced nutrient content and lowered consumer acceptance. A variety of antioxidant systems are known to reduce the overall oxidation of PUFAs. In certain exemplary embodiments, mixed tocopherols are provided in the liquid nutritional composition. In certain exemplary embodiments, mixed tocopherols are provided in an amount of about 200 ppm of the total oil in the liquid nutritional composition. In certain exemplary embodiments, ascorbyl palmitate is provided in the liquid nutritional composition. In certain exemplary embodiments, ascorbyl palmitate is provided in an amount of about 1200 ppm of the total oil content of the liquid nutritional composition.

In addition, in certain exemplary embodiments it is desirable to limit the amount of certain divalent cations in the liquid nutritional compositions. Divalent cations, as used herein, refer to at least one of iron, copper, and zinc. In certain exemplary embodiments, the liquid nutritional composition is substantially free of divalent cations. Substantially free, when used in this context, is intended to refer to a liquid nutritional composition wherein divalent cations are introduced to the liquid nutritional composition merely as inherent components of an intended ingredient (e.g., a contaminant). In certain exemplary embodiments, copper is present in an amount of less than 0.0004 mg/mL of the nutritional composition. In certain exemplary embodiments, copper is present in an amount of less than 0.0002 mg/mL of the nutritional composition. In certain exemplary embodiments, iron is present in an amount of less than 0.004 mg/mL of the nutritional composition. In certain exemplary embodiments, iron is present in an amount of less than 0.002 mg/mL of the nutritional composition. In certain exemplary embodiments, zinc is present in an amount of less than 0.025 mg/mL. In certain exemplary embodiments, zinc is present in an amount of less than 0.019 mg/mL.

In addition to DHA, in certain exemplary embodiments, the nutritional compositions include one or more additional PUFAs. Such additional PUFAs include, but are not limited to, arachidonic acid (AA), eicosapentaenoic acid (EPA), linoleic acid, linolenic acid (alpha linolenic acid), and gamma-linolenic acid. The PUFAs may be derived from oil sources such as plant oils, marine plankton, fungal oils, and fish oils.

Carotenoids

The nutritional compositions described herein include lutein. Lutein has been shown to provide oxidative protection, as well as to enhance brain development. The lutein may be provided as a part of a mixture of carotenoids or by itself. As used herein, the term "lutein" is intended to refer to all isomers of the compound. In certain exemplary embodiments, the nutritional compositions contain trans-lutein. As used herein, "trans-lutein" refers to a compound having the following structure:

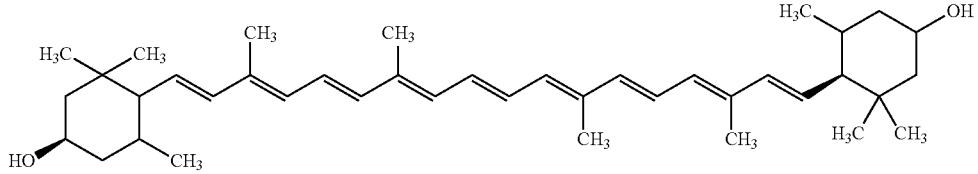 [SMILES: CC(/C=C/C=C(C)/C=C/C1C(C)C[C@@H](O)CC1(C)C)=C\C=C\C=C(C)\C=C\C=C(C)\C=C\[C@H]1C(C)CC(O)CC1(C)C]

In those embodiments where the nutritional composition includes trans-lutein, the nutritional composition can contain only trans-lutein or trans-lutein in combination with other lutein forms, or, in some aspects, the lutein is in all-trans form.

In certain exemplary embodiments, the nutritional compositions include one or more additional carotenoids such as beta-carotene, zeaxanthin, lycopene, and combinations thereof. It should be understood that any combination of beta-carotene, zeaxanthin, and lycopene can be included along with lutein in the nutritional compositions of the present disclosure.

The amount of lutein present in the nutritional compositions can vary depending on the individual, the intended use, or both. In certain exemplary embodiments, the lutein is present in the nutritional composition at a concentration effective to improve one or more of physical performance and cognition in an individual. In certain exemplary embodiments, the liquid nutritional composition comprises lutein in an amount of 0.3 mg to 35 mg per serving of the nutritional composition. In certain exemplary embodiments, the liquid nutritional composition comprises lutein in an amount of 0.3 mg to 20 mg per serving of the nutritional composition. In certain exemplary embodiments, the liquid nutritional composition comprises lutein in an amount of 0.5 mg to 20 mg per serving of the nutritional composition. In certain exemplary embodiments, the liquid nutritional composition comprises lutein in an amount of 1 mg to 20 mg per serving of the nutritional composition. In certain exemplary embodiments, the liquid nutritional composition comprises lutein in an amount of 2 mg to 20 mg per serving of the nutritional composition. In certain exemplary embodiments, the liquid nutritional composition comprises lutein in an amount of 3 mg to 20 mg per serving of the nutritional composition. In certain exemplary embodiments, the liquid nutritional composition comprises lutein in an amount of 4 mg to 20 mg per serving of the nutritional composition. In certain exemplary embodiments, the liquid nutritional composition comprises lutein in an amount of 5 mg to 20 mg per serving of the nutritional composition. In certain exemplary embodiments, the liquid nutritional composition comprises lutein in an amount of 6 mg to 20 mg per serving of the nutritional composition. In certain exemplary embodiments, the liquid nutritional composition comprises lutein in an amount of 0.3 mg to 10 mg per serving of the nutritional composition. In certain exemplary embodiments, the liquid nutritional composition comprises lutein in an amount of 0.3 mg to 9 mg per serving of the nutritional composition. In certain exemplary embodiments, the liquid nutritional composition comprises lutein in an amount of 0.3 mg to 8 mg per serving of the nutritional composition. In certain exemplary embodiments, the liquid nutritional composition comprises lutein in an amount of 0.3 mg to 7 mg per serving of the nutritional composition. In certain exemplary embodiments, the liquid nutritional composition comprises lutein in an amount of 0.3 mg to 6 mg per serving of the nutritional composition. In certain exemplary embodiments, the liquid nutritional composition comprises lutein in an amount of about 6 mg per serving of the nutritional composition.

Macronutrients

The nutritional compositions described herein include at least one of protein, fat, and carbohydrate. In certain exemplary embodiments, the nutritional composition includes protein, fat, and carbohydrate.

In certain exemplary embodiments, the nutritional composition contains protein, carbohydrate, and fat in proportions which are suitable for satisfying the nutritional needs of the individual for which they are intended. Such proportions are well known in the art, and any conventional proportion can be used. Thus, such compositions, when in a ready to use condition, typically contain concentrations of these macronutrients as set forth in Tables 1 and 2, with the percentages shown being based on the entire weight of each composition.

Table 1: Macronutrient profile for nutritional composition for muscle building formulations.

TABLE 1

|  | % weight based on entire composition | | | Calorie % | | |
| --- | --- | --- | --- | --- | --- | --- |
|  | Protein | Carbs | Fat | Protein | Carbs | Fat |
| Operative | 3-20 | 0.5-15 | 1-10 | 35-75 | 5-40 | 5-40 |
| Desirable | 5-15 | 1-10 | 0.3-5 | 45-70 | 10-35 | 10-35 |
| More Desirable | 6-10 | 2-6 | 0.5-2 | 40-65 | 15-30 | 15-30 |

TABLE 1-continued

|  | % weight based on entire composition | | | Calorie % | | |
| --- | --- | --- | --- | --- | --- | --- |
|  | Protein | Carbs | Fat | Protein | Carbs | Fat |
| Especially Desirable | 6-10 | 3-5 | 0.7-1.5 | 54-58 | 21-25 | 19-23 |

Table 2: Macronutrient profile for nutritional composition for adult supplement.

TABLE 2

|  | % weight based on entire composition | | | Calorie % | | |
| --- | --- | --- | --- | --- | --- | --- |
|  | Protein | Carbs | Fat | Protein | Carbs | Fat |
| Operative | 0.5-15 | 10-30 | 0.5-10 | 2-30 | 30-90 | 6-45 |
| Desirable | 1.4-8.5 | 11-25 | 1-7 | 6-25 | 40-80 | 10-40 |
| More Desirable | 2-7 | 13-24 | 1.5-6 | 10-20 | 45-75 | 15-35 |
| Especially Desirable | 2.9-5.8 | 14-20 | 2-5 | 12-17 | 50-70 | 20-31 |

Protein

In certain exemplary embodiments, the nutritional compositions described herein include a source or sources of protein. Any protein source that is suitable for use in oral liquid nutritional compositions and is compatible with the essential elements and features of such compositions is suitable for use herein.

The amount of protein present in the nutritional composition can vary widely and may be based on the particular needs of the intended consumer or the intended product form. Non-limiting examples of suitable proteins or sources thereof for use in the nutritional compositions include hydrolyzed, partially hydrolyzed, or non-hydrolyzed proteins or protein sources, which may be derived from any known or otherwise suitable source such as milk (e.g., casein, whey), animal (e.g., meat, fish), cereal (e.g., rice, corn), vegetable (e.g., soy, pea) or combinations thereof. Non-limiting examples of such proteins include milk protein isolates, milk protein concentrates, casein protein isolates, extensively hydrolyzed casein, sodium or calcium caseinates, whey protein, whey protein concentrates, whey protein isolate, whey protein hydrolysate, whole cow milk, partially or completely defatted milk, soy protein isolates, and soy protein concentrates. In certain exemplary embodiments, protein is present in an amount of 5 g to 20 g per serving of the nutritional composition. In certain exemplary embodiments, protein is present in an amount of 10 g to 20 g per serving of the nutritional composition. In certain exemplary embodiments, protein is present in an amount of 10 g to 15 g per serving of the nutritional composition. In certain exemplary embodiments, protein is present in an amount of 12 g to 14 g per serving of the nutritional composition. In certain exemplary embodiments, protein is present in an amount of about 13 g per serving of the nutritional composition. In certain exemplary embodiments, protein is present in an amount of about 0.05 g per mL of the nutritional composition.

Fat

In certain exemplary embodiments, the nutritional compositions described herein include a source or sources of fat in addition to DHA. Suitable sources of fat for use herein include any fat or fat source that is suitable for use in an oral liquid nutritional composition and is compatible with the essential elements and features of such formula.

The amount of fat present in the nutritional composition can vary widely and may be based on the particular needs of the intended consumer or the intended product form. Any fat or source thereof that is suitable for use in oral nutritional products and is compatible with the other ingredients of the inventive compositions can be used. Non-limiting examples of suitable fats or sources thereof for use in the nutritional compositions described herein include coconut oil, fractionated coconut oil, soy oil, corn oil, olive oil, safflower oil, high oleic safflower oil, MCT (medium chain triglycerides) oil, sunflower oil, high oleic sunflower oil, palm and palm kernel oils, palm olein, canola oil, high oleic canola oil, marine oils, fish oils, fungal oils, algae oils, cottonseed oils, and combinations thereof. In certain exemplary embodiments, fat is present in an amount of 3 g to 20 g per serving of the nutritional composition. In certain exemplary embodiments, fat is present in an amount of 5 g to 20 g per serving of the nutritional composition. In certain exemplary embodiments, fat is present in an amount of 5 g to 10 g per serving of the nutritional composition. In certain exemplary embodiments, fat is present in an amount of 6 g to 9 g per serving of the nutritional composition. In certain exemplary embodiments, fat is present in an amount of about 7.5 g per serving of the nutritional composition. In certain exemplary embodiments, fat is present in an amount of less than 8 g per serving of the nutritional composition. In certain exemplary embodiments, fat is present in an amount of about 0.03 g per mL of the nutritional composition.

Carbohydrate

In certain exemplary embodiments, the nutritional compositions described herein include a source or sources of carbohydrate. Any carbohydrate source that is suitable for use in oral liquid nutritional compositions and is compatible with the essential elements and features of such compositions is suitable for use herein.

The amount of carbohydrate present in the nutritional composition can vary widely and may be based on the particular needs of the intended consumer or the intended product form. Any carbohydrate or source thereof that is suitable for use in oral nutritional products and is compatible with the other ingredients of the inventive compositions can be used as the carbohydrate in the nutritional compositions. Non-limiting examples of a source of carbohydrate suitable for use in the nutritional compositions described herein include maltodextrin, hydrolyzed or modified starch or cornstarch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol), isomaltulose, sucromalt, pullulan, potato starch, slowly-digested carbohydrates, dietary fibers (e.g., oat fiber, soy fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinogalactans, glucomannan, xanthan gum, alginate, pectin, low and high methoxy pectin, cereal beta-glucans (e.g., oat beta-glucan, barley beta-glucan), carrageenan and psyllium), Fibersol™, other resistant starches, and combinations thereof.

In certain applications, it is desirable to provide a nutritional composition with a relatively lower level of carbohydrates. In certain exemplary embodiments, the liquid nutritional composition has up to 60 g (i.e., 0-60 g) of carbohydrate per serving. In certain exemplary embodiments, the liquid nutritional composition has less than 50 g (i.e., 0-50 g) of carbohydrate per serving. In certain exemplary embodiments, the liquid nutritional composition has less than 45 g of carbohydrate per serving. In certain exemplary embodiments, the liquid nutritional composition has less than 40 g of carbohydrate per serving. An alternative way of expressing the amount of carbohydrate in a nutritional composition is grams of carbohydrate per mL. Therefore, in certain exemplary embodiments, the liquid nutritional composition comprises less than 0.21 g/mL of carbohydrate. In certain exemplary embodiments, the liquid nutritional composition comprises less than 0.20 g/mL of carbohydrate. In certain exemplary embodiments, the liquid nutritional composition comprises less than 0.17 g/mL of carbohydrate (i.e., less than 40 g/237 mL serving).

Generally, liquid nutritional compositions that comprise high levels of protein (i.e., above 0.042 g/mL) demonstrate better shelf stability when the higher protein content is paired with a higher fat content (i.e., above 0.03 g/mL). In certain instances, a weight ratio of fat to protein of greater than 0.8, including greater than 0.9 is recommended to achieve desired levels of consumer acceptance. Surprisingly, the liquid nutritional compositions according to the general inventive concepts achieve consumer acceptability scores in line with those of conventional liquid nutritional compositions, while providing a relatively high level of protein (e.g., about 13 g per serving) in conjunction with a lower level of fat (e.g., about 8 g per serving or less). In certain exemplary embodiments, the liquid nutritional composition comprises a source of protein and a source of fat, and has a weight ratio of fat to protein of less than 0.8. In certain exemplary embodiments, the weight ratio of fat to protein is less than 0.7. In certain exemplary embodiments, the weight ratio of fat to protein is less than 0.6. In certain exemplary embodiments, the weight ratio of fat to protein is about 0.55.

Table 3 shows an inventive liquid nutritional composition in comparison to several conventional liquid nutritional compositions.

TABLE 3

| Nutrient | Inventive Formulation | Conventional Formulation 1 | Conventional Formulation 2 | Conventional Formulation 3 |
| --- | --- | --- | --- | --- |
| Calories | 260 | 350 | 350 | 220 |
| Protein | 13 | 13 | 13 | 9 |
| HMB | 1.5 | 1.5 | 0 | 0 |
| Fat | 7.5 | 11 | 11 | 6 |
| Carbohydrates | 38 | 51 | 50 | 32 |
| Sugars | 10 | 20 | 20 | 15 |
| Lutein | 6 | 0 | 0 | 0 |
| DHA | 125 | 0 | 0 | 0 |

Optional Ingredients

In certain exemplary embodiments, the nutritional composition may further comprise other optional ingredients that may modify its physical, chemical, hedonic, or processing characteristics or serve as pharmaceutical or additional nutritional components when used in the targeted population. Many such optional ingredients are known or otherwise suitable for use in other nutritional compositions and may also be used in the nutritional compositions described herein, provided that such optional ingredients are safe and effective for oral administration and are compatible with the essential and other ingredients in the selected product form.

Different sources and types of proteins, carbohydrates, fats, vitamins, and minerals are known and may be used in the exemplary embodiments disclosed or suggested herein, provided that such nutrients are compatible with the other ingredients in the selected nutritional composition, are safe for their intended use, and do not otherwise unduly impair product performance.

In certain exemplary embodiments, the nutritional composition further comprises any of a variety of vitamins or related nutrients, non-limiting examples of which include vitamin A, vitamin D, vitamin E, vitamin K, thiamine, riboflavin, vitamin B6, vitamin B12, carotenoids, niacin, folic acid, pantothenic acid, biotin, vitamin C, choline, inositol, salts, and derivatives thereof, and combinations thereof.

In certain exemplary embodiments, the nutritional composition further comprises any of a variety of minerals, non-limiting examples of which include phosphorus, magnesium, calcium, manganese, sodium, potassium, molybdenum, chromium, selenium, chloride, iodide, and combinations thereof.

In certain exemplary embodiments, the nutritional composition may be an "excellent source of" (as defined by the Food and Drug Administration) at least one of the following: calcium, riboflavin, vitamin B6, folate, pantothenic acid, phosphorous, iodine, selenium, manganese, chromium, molybdenum, and combinations thereof.

In certain exemplary embodiments, the nutritional composition may be a "good source of" (as defined by the Food and Drug Administration) at least one of the following: vitamin A, vitamin C, vitamin E, thiamin, niacin, biotin, and combinations thereof.

Non-limiting examples of other optional ingredients include fiber, preservatives, additional antioxidants, emulsifying agents, buffers, colorants, flavors, probiotics, prebiotics, thickening agents and stabilizers, and so forth.

In certain exemplary embodiments, the nutritional composition comprises at least one sweetening agent. In certain exemplary embodiments, the at least one sweetening agent is a sugar alcohol such as maltitol, erythritol, sorbitol, xylitol, mannitol, isolmalt, lactitol, and combinations thereof, or at least one artificial or high potency sweetener such as acesulfame K, aspartame, sucralose, saccharin, stevia, tagatose, monk fruit, and combinations thereof. The sweetening agents, especially as a combination of a sugar alcohol and an artificial sweetener, may be especially useful in formulating nutritional compositions having a desirable flavor profile. In certain exemplary embodiments, the nutritional composition may comprise at least one sugar alcohol with a concentration of from at least 0.01%, including from about 0.1% to about 10%, and also including from about 1% to about 6% by weight of the nutritional composition. In certain exemplary embodiments, the nutritional composition may comprise at least one artificial sweetener with a concentration of from 0.01% to 5%, including from 0.05% to 3%, and also including from 0.1% to 1% by weight of the nutritional composition.

In certain exemplary embodiments, the nutritional composition comprises a stabilizer. Any stabilizer that is known or otherwise suitable for use in a nutritional composition may be suitable for use herein, some non-limiting examples of which include gums such as carrageenan and xanthan gum. In certain exemplary embodiments, the stabilizer may represent from about 0.1% to about 5%, including from about 0.5% to about 3%, and including from about 0.7% to about 1.5% by weight of the nutritional composition.

In certain exemplary embodiments, the nutritional composition comprises one or more masking agents to reduce or otherwise obscure the effects of any bitter flavors and after taste that may develop in the nutritional composition over time. Suitable masking agents include natural and artificial sweeteners, sodium sources such as sodium chloride, and combinations thereof. The amount of masking agent added to the nutritional composition may vary depending upon the particular masking agent selected, other ingredients in the formulation, and other formulation or product target variables. Such amounts, however, can range from about 0.1% to about 3%, including from about 0.15% to about 3%, and also including from about 0.2% to about 2.5%, by weight of the nutritional composition.

The various nutritional compositions disclosed herein, as well as other embodiments contemplated by the general inventive concepts, may be prepared by any process or suitable method (now known or known in the future) for making a selected product form, such as a nutritional liquid, a nutritional solid, or a nutritional powder. Many such techniques are known for any given product form and can easily be applied by one of ordinary skill in the art to the various embodiments presented herein.

According to certain exemplary embodiments, the composition comprising a combination of a source of HMB, DHA, and lutein is formulated as, and intended for consumption in, any known or otherwise suitable oral product form. Any solid, liquid, semi-solid, semi-liquid, or powder product form, including combinations or variations thereof, are suitable for use herein, provided that such forms allow for safe and effective oral delivery to the individual via oral consumption of the ingredients as also defined herein.

In certain exemplary embodiments, the nutritional composition is a solid nutritional product. Non-limiting examples of solid nutritional products include snack and meal replacement products, including those formulated as bars; sticks; cookies, breads, cakes, other baked goods; frozen liquids; candy; breakfast cereals; powders, granulated solids, or other particulates; snack chips or bites; frozen or retorted entrees; and so forth.

In certain exemplary embodiments, the nutritional composition is a nutritional liquid. Non-limiting examples of nutritional liquids include snack and meal replacement products, hot or cold beverages, carbonated or non-carbonated beverages, juices or other acidified beverages, milk or soy-based beverages, shakes, coffees, teas, compositions for administration by nasogastric intubation, and so forth. Generally, the nutritional liquids are formulated as suspensions or emulsions, but the nutritional liquids can also be formulated in other suitable forms such as clear liquids, solutions, liquid gels, liquid yogurts, and so forth.

In certain exemplary embodiments, where the nutritional composition is a liquid, a serving of the nutritional liquid is within a range of 30 milliliters to 500 milliliters (~1 fl. oz. to ~17 fl. oz.). In certain exemplary embodiments, the serving is 177 milliliters to 417 milliliters (~6 fl. oz. to ~14 fl. oz.), including 207 milliliters to 266 milliliters (~7 fl. oz. to ~9 fl. oz.). In certain exemplary embodiments, the serving is 237 milliliters (~8 fl. oz.) In certain exemplary embodiments, where the nutritional composition is administered as a liquid, one serving to four servings of the nutritional composition may be administered to the individual per day.

The nutritional compositions disclosed herein are useful to provide sole, primary, or supplemental sources of nutrition, as well as providing one or more of the benefits as described herein. In certain exemplary embodiments, the nutritional composition provides up to 1000 kcal of energy per serving or dose, including from 20 kcal to 900 kcal, from 40 kcal to 700 kcal, from 50 kcal to 500 kcal, from 150 kcal to 475 kcal, from 200 kcal to 450 kcal, or from 200 kcal to 350 kcal per serving. In certain exemplary embodiments, the nutritional composition provides about 260 kcal per serving.

Another way of expressing the caloric content of a nutritional composition is the number of calories per mL of liquid. In certain exemplary embodiments, the nutritional composition provides less than 1.4 kcal/mL. In certain exemplary embodiments, the nutritional composition provides up to 1.3 kcal/mL, including from 1.0 kcal/mL to 1.25 kcal/mL, including from 1.0 kcal/mL to 1.2 kcal/mL, including from 1.0 kcal/mL to 1.15 kcal/mL, and including from 1.0 kcal/mL to about 1.1 kcal/mL. In certain exemplary embodiments, the nutritional composition provides about 1.1 kcal/mL.

In accordance with certain exemplary embodiments, the effective amount of the composition comprising a combination of HMB, DHA, and lutein can be administered to the individual one or more times per day for a period of up to three weeks, or for a period of at least three weeks, to achieve the desired effect. For example, a composition comprising a combination of HMB, DHA, and lutein can be administered to an individual every day for at least three weeks, every day for at least four weeks, every day for at least eight weeks, every day for at least six months, or every day for a year or more. Within the context of providing a dose or serving to an individual, every day is intended to reflect a period of administration wherein an individual has been instructed to be administered the composition every day, and wherein the individual actually is administered the composition for at least 70% (and in certain embodiments at least 90%) of the days during the period of administration.

As used herein, "regular intervals" refers to administration in a repeating, periodic fashion where the time between administrations is approximately (or intended to be approximately) the same. In various embodiments, administration at regular intervals includes daily administration or weekly administration. In further embodiments, the term "regular intervals" refers to administration 1-2 times per week, administration 1-3 times per week, administration 2-3 times per week, administration 1-4 times per week, administration 1-5 times per week, administration 2-5 times per week, administration 3-5 times per week, administration 1-6 times per week, administration 1-7 times per week, administration 2-6 times per week, administration 2-7 times per week, administration 1-2 times per day, administration 1-3 times per day, administration 1-4 times per day, administration 2-3 times per day, administration 2-4 times per day, administration 3-4 times per day, administration 2-5 times per day, administration 3-5 times per day, or administration 4-5 times per day.

Methods of Manufacture

In certain exemplary embodiments, the nutritional compositions may be manufactured by any known or otherwise suitable method. Inventive nutritional compositions in liquid form may be suitably sterilized, for example, by aseptic sterilization or retort sterilization.

In those embodiments in which the nutritional compositions are in the form of a nutrition shake, they may be prepared by any of the well known methods of formulating such compositions by way of retort, aseptic packaging, or hot fill processing methods.

For example, in one suitable manufacturing process for formulating a nutrition shake, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, DHA) and then adding an emulsifier (e.g., lecithin), fat soluble vitamins, and a portion of the total protein with continued heat and agitation. The CHO-MIN slurry is formed by adding with heated agitation to water: minerals (e.g., HMB, potassium citrate, dipotassium phosphate, sodium citrate), trace and ultra trace minerals (TM/UTM premix), thickening or suspending agent. The resulting CHO-MIN slurry is held for 10 minutes with continued heat and agitation before adding additional minerals (e.g., potassium chloride, magnesium carbonate, potassium iodide), and/or carbohydrates (e.g., sucrose, corn syrup). The PIW slurry is then formed by mixing with heat and agitation the remaining protein, if any. Those of skill in the art will recognize that other exemplary methods exist for combining the necessary ingredients, for example, in one exemplary embodiment, the protein is mixed into the PIW slurry, and thus only two slurries are used in the process.

The resulting slurries are then blended together with heated agitation and the pH adjusted to 6.9-7.1, after which the composition is subjected to ultra high temperature (UHT) processing during which the composition is heat treated, emulsified, and homogenized and then allowed to cool. Water soluble vitamins and ascorbic acid are added, the pH is adjusted to the desired range if necessary, flavors are added, and water is added to achieve the desired total solid level. The composition may then be aseptically packaged to form an aseptically packaged nutritional emulsion.

The following examples further describe and demonstrate specific embodiments within the scope of the general inventive concepts. The examples are given solely for the purpose of illustration and are not to be construed as limitations of the present invention, as many variations thereof are possible without departing from the spirit and scope of the invention. All exemplified amounts are weight percentages based upon the total weight of the composition, unless otherwise specified.

Methods of Use

The methods of use of the present disclosure include the oral administration of nutritional compositions that include HMB, DHA, and lutein to improve at least one of physical performance and cognition.

In certain exemplary embodiments, improvement or enhancement of at least one of physical performance and cognition is measured by analysis of a biological sample from the individual. In certain exemplary embodiments, biomarkers associated with at least one of physical performance and cognition are measured to determine improvement or enhancement of at least one of physical performance and cognition. In certain exemplary embodiments, the biomarkers include, but are not limited to cortisol, DHEAS, norepinephrine, lactate, serotonin, orexin, NPY, etc. In certain exemplary embodiments, the biomarkers are measured by one of enzyme-linked immunosorbent assay and radioimmunoas say procedures.

In certain exemplary embodiments, the nutritional compositions disclosed herein are useful for enhancing physical performance in an individual. Physical performance can be categorized and tested in a variety of ways. Major categories of physical performance include body composition, muscle strength, endurance, and muscle mass. As used herein, the phrase "improving physical performance" should be understood to include one or more of improving body composition, improving endurance, improving muscle function, maintaining muscle mass, increasing muscle mass, and reducing fat mass.

In certain exemplary embodiments, improvement or enhancement of physical performance such as body composition, muscle strength, endurance, and muscle mass is assessed relative to the physical performance before beginning treatment. In another embodiment, improvement or enhancement of body composition, muscle strength, endurance, and muscle mass is assessed relative to an untreated subject. In another embodiment, improvement or enhancement of body composition, muscle strength, endurance, and muscle mass is assessed according to a standardized criterion such as, for example, a physical performance test or the like.

The body composition of an individual may be determined by a wide variety of methods. For example, body composition may be determined by techniques including, but not limited to, bioelectrical impedance analysis (BIA), air displacement plethysmography (ADP), hydrodensitometry, dual energy x-ray absorptiometry (DEXA), densitometry, magnetic resonance imaging (MRI), and computed tomography (CT). Furthermore, skeletal muscle mass, area, volume, density, or total body protein of an individual may be determined by a wide variety of methods. For example, skeletal muscle mass, area, or volume may be determined by techniques including, but not limited to, dual energy x-ray absorptiometry (DEXA), densitometry, magnetic resonance imaging (MRI), computed tomography (CT), bioelectrical impedance analysis (BIA), bioelectrical impedance spectroscopy (BIS), and skin-fold thickness. Moreover, total body protein, which is the functional mass of muscle, may be computed from an algorithm based on the combination of DEXA and BIA values (Wilson J P et al., *Am. J. Clin Nutr.*, (March 2013), Vol. 97, No. 3, pp. 497-504).

Muscle function in an individual may be evaluated by a wide variety of methods. For example, muscle function in terms of muscle mass in an individual may be determined by using any known or otherwise effective technique that provides muscle area, volume, or mass, such as DEXA, or using visual or imaging techniques such as MRI or CT scans. In addition, muscle function in an individual in terms of muscle strength can be quantitatively measured using acute tests of maximum force, time-dependent tests of muscle endurance, time-dependent tests of muscle fatigue, time-dependent tests of muscle endurance and fatigue, and combinations thereof. Furthermore, muscle function in an individual may be measured by using a grip meter, by evaluating lower extremity strength using equipment to measure isokinetic knee extensor or knee flexor strength, and by measuring gait and balance (e.g., via the Tinetti Gait and Balance test).

In certain exemplary embodiments, an improvement or enhancement in physical performance is determined by measuring an individual's performance in, for example, a ParvoMedics TrueOne 2400 Metabolic Measurement System to determine aerobic fitness. In certain exemplary embodiments, the aerobic fitness is determined using a treadmill running test. In certain exemplary embodiments, the aerobic fitness is determined by measuring an individual's $VO_2$ max. In certain exemplary embodiments, an improvement or enhancement in physical performance is determined by measuring blood pressure, including resting BP and/or heart rate during exercise. In certain exemplary embodiments, an improvement or enhancement in physical performance is determined by measuring heart rate, including resting heart rate and/or heart rate during exercise. In certain exemplary embodiments, an improvement or enhancement in physical performance is determined by measuring visual-motor skills, including but not limited to visuo-motor reaction time using a set of pre-programmed assessment tests. In certain exemplary embodiments, an improvement or enhancement in physical performance is determined by measuring an individual's performance in a balance test, including but not limited to a Y-Balance Test.

In certain exemplary embodiments, an improvement or enhancement in physical performance is determined by measuring the vertical jump of an individual. In certain exemplary embodiments, an improvement or enhancement in physical performance is determined by measuring the maximum number of push-ups performed by an individual in a predetermined amount of time. In certain exemplary embodiments, an improvement or enhancement in physical performance is determined by measuring the maximum number of sit-ups performed by an individual in a predetermined amount of time. In certain exemplary embodiments, an improvement or enhancement in physical performance is determined by measuring the maximum number of pull-ups performed by an individual in a predetermined amount of time. In certain exemplary embodiments, an improvement or enhancement in physical performance is determined by measuring an individual's performance in one or more functional exercises including, but not limited to, a run of a predetermined distance (e.g., 1.5 mile), standing long jump, sled push, weight carry, and an agility test.

In certain exemplary embodiments, administration of the nutritional compositions disclosed herein result in an improvement or enhancement in physical performance of an individual. For example, in an exemplary embodiment, administering a composition comprising HMB, DHA, and lutein to an individual can improve the individual's physical performance by at least 10%, such as 10% to 100%, including 20% to 100%, including 30% to 100%, including 40% to 100%, including 50% to 100%, including 60% to 100%, including 70% to 100%, including 80% to 100%, including 90% to 100%, and including greater than 100% improvement.

In certain exemplary embodiments, the nutritional compositions disclosed herein are useful for enhancing cognitive function in an individual. Cognitive function can be categorized and tested in a variety of ways. Major categories of cognitive function include memory and intelligence. However, a wide variety of more complex cognitive functions are known. These include verbal memory, implicit memory and learning, and those supported by our ability to organize information, such as executive function. In certain exemplary embodiments, an improvement or enhancement in cognition is determined by measuring an individual's performance in a cognitive test.

In certain exemplary embodiments, administration of the nutritional compositions disclosed herein result in an improvement in cognitive function of an individual. For example, in an exemplary embodiment, administering a composition comprising HMB, DHA, and lutein to an individual can improve the individual's cognitive function by at least 10%, such as 10% to 100%, including 20% to 100%, including 30% to 100%, including 40% to 100%, including 50% to 100%, including 60% to 100%, including 70% to 100%, including 80% to 100%, including 90% to 100%, and including greater than 100% improvement.

In certain exemplary embodiments, improvement or enhancement of a cognitive function such as focus, attention, alertness, memory or intelligence is assessed relative to the cognitive memory, or intelligence before beginning treatment. In another embodiment, improvement or enhancement of focus, attention, alertness, cognitive memory, or intelligence is assessed relative to an untreated subject. In another embodiment, improvement or enhancement of focus, attention, alertness, cognitive memory, or intelligence is assessed according to a standardized criterion such as, for example, a test or the like.

In certain exemplary embodiments, an improvement or enhancement in cognition is determined by measuring an individual's performance in the Illinois Cognitive Function Battery (ICFB). The ICFB is a series of computer-based cognitive performance tests. Examples of testing in the ICFB include, but are not limited to, number sets, letter sets, digit span, rotational span, decision making, keeping track (executive function), paired associates, immediate free recall, and delayed picture recall.

In addition to the specific measurements described above, in certain exemplary embodiments, an improvement or enhancement of at least one of physical performance and cognition is measured by a survey completed by the individual. In certain exemplary embodiments, an improvement or enhancement of at least one of physical performance and cognition is measured by a test to determine at least one of life stress, personality hardiness, resilience (recovery from stress), motivation, and personality factors (e.g., neuroticism, agreeableness, conscientiousness, extraversion, openness, etc.).

EXAMPLES

The following examples illustrate certain embodiments or features of compositions and methods described herein. The examples are given solely for the purpose of illustration and are not to be construed as limitations of the general inventive concepts, as many variations thereof are possible without departing from the spirit and scope of the disclosure.

Table 4 shows a Bill of Materials for a liquid nutritional composition formulated according to the general inventive concepts.

TABLE 4

| Ingredient | Unit | 100 lb |
| --- | --- | --- |
| Ingredient Water | lb | 74.98 |
| Sucrose | lb | 8.20 |
| Maltrin M100 | lb | 5.75 |
| Sodium caseinate | lb | 2.62 |
| Milk Protein Concentrate 80% | lb | 1.82 |
| Canola Oil | lb | 1.62 |
| Soy Protein Isolate | lb | 1.19 |
| Corn Oil | lb | 0.85 |
| Calcium HMB | lb | 0.65 |
| Potassium Citrate | lb | 0.49 |
| Whey Protein Concentrate | lb | 0.30 |
| Magnesium Phosphate Dibasic | lb | 0.27 |
| Avicel CL611 | lb | 0.24 |
| Soy Lecithin | lb | 0.18 |
| Artificial Flavor | lb | 0.15 |
| DHASCO (45% DHA) | lb | 0.13 |
| Sodium Citrate | lb | 0.12 |
| Artificial flavor | lb | 0.1 |
| Artificial Flavor | lb | 0.1 |
| Choline Chloride | g | 30.00 |
| Ascorbic Acid | g | 21.09 |
| 45% KOH | g | 14.65 |
| Zinc Sulfate | g | 10.00 |
| Viscarin SA-359 | g | 6.80 |
| 20% Lutein in Safflower oil - FloraGLO | g | 6.04 |
| Carrageenan - 100229 | g | 3.86 |
| WSV Vitamin premix | g | 3.28 |
| Vitamin E (RRR-d-alpha) Tocopheryl Acetate- 1.36 IU/mg | g | 1.50 |
| Ascorbyl Palmitate | g | 1.45 |
| FD&C Red #3 | g | 0.36 |
| Pyridoxine Hydrochloride (B6), USP | g | 0.30 |
| Tocopherol-2 antioxidant | g | 0.24 |
| Vit D3 oil soluble | g | 0.11 |

TABLE 4-continued

| Ingredient | Unit | 100 lb |
| --- | --- | --- |
| Folic Acid, USP | g | 0.08 |
| Sodium Selenate | g | 0.04 |
| Potassium Iodide | g | 0.0094 |
| Cyanocobalamin (B12), USP | g | 0.0011 |

Table 5 shows the measured composition of a liquid nutritional composition according to Table 4.

TABLE 5

| Component | Unit of Measure | Result |
| --- | --- | --- |
| Ash | % | 1.07 |
| Total solids | % | 24.12 |
| Fat | % | 2.91 |
| Protein | % | 5.14 |
| Density | g/ml | 1.0796 |
| Ca | mg/100 g | 124 |
| Cu | mg/100 g | 0.018 |
| Fe | mg/100 g | 0.19 |
| K | mg/100 g | 266 |
| Mg | mg/100 g | 41.1 |
| Mn | mg/100 g | 0.0181 |
| Na | mg/100 g | 90.4 |
| P | mg/100 g | 106 |
| Zn | mg/100 g | 1.96 |
| Cr | meg/kg | 22.1 |
| Mo | meg/kg | 48.6 |
| Se | meg/kg | 113 |
| DHA | mg/100 g | 50 |
| Lutein | mg/100 g | 2.4 |

In certain exemplary embodiments, the nutritional compositions described herein are shelf stable. Shelf stability may be measured in a variety of ways, but generally refers to a composition that remains commercially viable for a period of time, such as 3 to 24 months, during storage. Commercially viable relates to consumer acceptance and may be measured by well known hedonic or organoleptic testing. One particular method is grain score. Table 6 shows the results of several organoleptic endpoints for a nutritional composition formulated according to the general inventive concepts.

TABLE 6

| Test | Unit of Measure | Result |
| --- | --- | --- |
| Grain Score | 1 best, 6 worst | 1 |
| pH | 1-14 | 6.98 |
| Viscosity | cP | 22.7 |

Table 7 shows the results of a consumer sensory evaluation of a variety of liquid nutritional compositions formulated according to the general inventive concepts.

TABLE 7

| | Overall Liking for Flavor | Color Appropriate for Flavor | Rank Preference |
| --- | --- | --- | --- |
| Vanilla, commercial retort control | 5.1 c | 5.8 c | 3.0 b |
| Vanilla, aseptic control, no DHA/Lutein | 5.7 b | 7.6 a | 2.7 ab |
| Vanilla, aseptic control, DHA/Lutein added | 4.8 c | 5.3 d | 3.7 c |

TABLE 7-continued

|  | Overall Liking for Flavor | Color Appropriate for Flavor | Rank Preference |
|---|---|---|---|
| Banana, aseptic prototype with DHA and | 6.0 ab | 6.4 b | 2.6 ab |
| Peach, aseptic prototype with DHA and | 6.2 a | 6.1 be | 2.2 a |
| statistical information scale | p-value: <0.0001<br>LSD: 0.44<br>5 = Neither like nor dislike<br>6 = Like slightly<br>7 = Like moderately | p-value: <0.0001<br>LSD: 0.47<br>1 = Not at all appropriate<br>9 = Extremely appropriate | p-value: 0.0001<br>LSD: 0.65<br>1 = Most preferred<br>5 = Least preferred |

All percentages, parts and ratios as used herein, are by weight of the total composition, unless otherwise specified. All such weights as they pertain to listed ingredients are based on the active level and, therefore, do not include solvents or by-products that may be included in commercially available materials, unless otherwise specified.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range.

All references to singular characteristics or limitations of the present disclosure shall include the corresponding plural characteristic or limitation, and vice versa, unless otherwise specified or clearly implied to the contrary by the context in which the reference is made.

The various embodiments of the nutritional composition of the present disclosure may also be substantially free of any ingredient or feature described herein, provided that the remaining nutritional composition still contains all of the required ingredients or features as described herein. In this context, and unless otherwise specified, the term "substantially free" means that the selected composition contains less than a functional amount of the optional ingredient, typically less than 1%, including less than 0.5%, including less than 0.1%, and also including zero percent, by weight of such optional ingredient.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the application, in its broader aspects, is not limited to the specific details, the representative compositions and processes, and illustrative examples shown and described. Accordingly, departures may be made from such details without departing from the spirit or scope of the general inventive concepts.

What is claimed is:

1. A liquid nutritional composition comprising, per 237 ml serving:
   beta-hydroxy-beta-methylbutyrate (HMB) in an amount of 0.25 g to 3 g;
   fat comprising docosahexaenoic acid (DHA), wherein the DHA is in an amount of 32 mg to 2500 mg;
   lutein in an amount of 0.3 mg to 35 mg; and
   10 g to 20 g of protein;
   wherein a weight ratio of the fat to the protein is from 0.55 to less than 0.8; and
   wherein the liquid nutritional composition comprises an oil-in-water emulsion.

2. The liquid nutritional composition of claim 1, wherein the protein comprises milk protein isolate, milk protein concentrate, casein protein isolate, extensively hydrolyzed casein, sodium or calcium caseinate, whey protein, whey protein concentrate, whey protein isolate, whey protein hydrosylate, whole cow milk, partially or completely defatted milk, soy protein isolate, soy protein concentrate, or a combination thereof.

3. The liquid nutritional composition of claim 1, wherein the fat further comprises coconut oil, fractionated coconut oil, soy oil, corn oil, olive oil, safflower oil, high oleic safflower oil, MCT (medium chain triglycerides) oil, sunflower oil, high oleic sunflower oil, palm oil, palm kernel oil, palm olein, canola oil, high oleic canola oil, marine oil, fish oil, fungal oil, algae oil, cottonseed oil, or a combination thereof.

4. The liquid nutritional composition of claim 1, further comprising copper, wherein the copper is present in an amount of less than 0.0004 mg per mL of the liquid nutritional composition.

5. The liquid nutritional composition of claim 4, wherein the copper is present in an amount of less than 0.0002 mg per mL of the liquid nutritional composition.

6. The liquid nutritional composition of claim 1, further comprising iron, wherein the iron is present in an amount of less than 0.004 mg per mL of the liquid nutritional composition.

7. The liquid nutritional composition of claim 6, wherein the iron is present in an amount of less than 0.002 mg per mL of the liquid nutritional composition.

8. The liquid nutritional composition of claim 1, further comprising zinc, wherein the zinc is present in an amount of less than 0.025 mg/mL.

9. The liquid nutritional composition of claim 8, wherein the zinc is present in an amount of less than 0.019 mg/m L.

10. The liquid nutritional composition of claim 1, wherein the liquid nutritional composition has a caloric density of less than 1.4 kcal/mL.

11. The liquid nutritional composition of claim 1, wherein the liquid nutritional composition has a caloric density of from 1.05 to 1.4 kcal/m L.

12. The liquid nutritional composition of claim 1, further comprising carbohydrate in an amount of less than 60 g in the serving of the liquid nutritional composition.

13. A liquid nutritional composition comprising, per 237 ml serving:
- beta-hydroxy beta-methylbutyrate (HMB) in an amount of 0.25 g to 3 g;
- fat comprising docosahexaenoic acid (DHA), wherein the DHA is in an amount of 32 mg to 2500 mg;
- lutein in an amount of 0.3 mg to 20 mg; and
- 10 g to 20 g of protein;
- wherein a weight ratio of the fat to the protein is from 0.55 to less than 0.8; and
- wherein the liquid nutritional composition comprises an oil-in-water emulsion.

14. The liquid nutritional composition of claim 13, wherein the HMB is present in an amount of 1 g to 3 g in the serving of the liquid nutritional composition.

15. The liquid nutritional composition of claim 13, wherein the HMB is present in an amount of about 1.5 g in the serving of the liquid nutritional composition.

16. The liquid nutritional composition of claim 13, wherein the HMB is calcium HMB.

17. The liquid nutritional composition of claim 13, wherein the DHA is present in an amount of 50 mg to 1000 mg in the serving of the liquid nutritional composition.

18. The liquid nutritional composition of claim 13, wherein the DHA is present in an amount of about 125 mg in the serving of the liquid nutritional composition.

19. The liquid nutritional composition of claim 13, wherein the lutein is present in an amount of 0.3 mg to 10 mg in the serving of the liquid nutritional composition.

20. The liquid nutritional composition of claim 13, wherein the lutein is present in an amount of about 6 mg in the serving of the liquid nutritional composition.

21. A liquid nutritional composition comprising, per 237 ml serving:
- beta-hydroxy-beta-methylbutyrate (HMB) in an amount of 1 g to 2.5 g;
- fat comprising docosahexaenoic acid (DHA), wherein the DHA is in an amount of 50 mg to 150 mg;
- lutein in an amount of 5 mg to 8 mg;
- 10 g to 15 g of protein; and
- 6 g to 9 g of the fat; and
- wherein a weight ratio of the fat to the protein is from 0.55 to less than 0.8; and
- wherein the liquid nutritional composition comprises an oil-in-water emulsion.

22. The liquid nutritional composition of claim 1, wherein the weight ratio of the fat to the protein is from 0.55 to less than 0.7.

* * * * *